US006982364B1

(12) United States Patent
Osteryoung

(10) Patent No.: US 6,982,364 B1
(45) Date of Patent: Jan. 3, 2006

(54) MANIPULATION OF A MIND GENE IN PLANTS TO ALTER PLASTID SIZE, SHAPE AND/OR NUMBER

(75) Inventor: Katherine W. Osteryoung, Williamston, MI (US)

(73) Assignee: University and Community College System of Nevada, Reno, NV (US)

( * ) Notice: Subject to any disclaimer, the term of this patent is extended or adjusted under 35 U.S.C. 154(b) by 0 days.

(21) Appl. No.: 09/553,431

(22) Filed: Apr. 19, 2000

Related U.S. Application Data

(60) Provisional application No. 60/130,403, filed on Apr. 19, 1999.

(51) Int. Cl.
A01H 5/00 (2006.01)
A01H 5/10 (2006.01)
C12N 15/82 (2006.01)
C12N 15/29 (2006.01)

(52) U.S. Cl. .................... 800/298; 800/278; 536/23.6
(58) Field of Classification Search ................ 800/278, 800/290, 298; 435/419; 536/23.6
See application file for complete search history.

(56) References Cited

U.S. PATENT DOCUMENTS 5,981,836 A    11/1999    Osteryoung

OTHER PUBLICATIONS

Sato, S. et al., "Structural Analysis of *Arabidopsis thaliana* Chromosome 5. IV. Sequence Features of the Regions of 1,456,315 bp Covered by Nineteen Physically Assigned P1 and TAC Clones." 1998, DNA Research, vol. 5, pp. 41-54.*
Sweetlove, L. J. et al., "Starch metabolism in tubers of transgenic potato (*Solanum tuberosum*) with increased ADPglucose pyrophosphorylase." 1996, Biochem. J., vol. 320, pp. 493-498.*

Hill, M. A. and Preiss, J. "Functional Analysis of Conserved Histidines in ADP-Glucose Pyrophosphorylase from *Escherichia coli*." 1998, Biochemical and Biophysical Res. Comm., vol. 244, pp. 573-577.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247-1252.*
Nakamura, Y., Accession No. AB009056, 1997.*
Tang, G. et al., "Antisense Repression of Vacuolar and Cell Wall Invertase in Transgenic Carrot Alters Early Plant Development and Sucrose Partitioning." 1999, The Plant Cell, vol. 11, pp. 177-189.*
Klann, E. M. et al., "Antisense Acid Invertase (TIV1) Gene Alters Soluble Sugar Composition and Size in Transgenic Tomato Fruit." 1996, Plant Physiol., vol. 112, pp. 1321-1330.*
Colliver, S. P. et al., "Differential modification of flavonoid and isoflavonoid biosynthesis with an antisense chalcone synthase contruct in transgenic *Lotus corniculatus*." 1997, Plant Molecular Biology, vol. 35, pp. 509-522.*
Collette, et al., "A homologue of the bacterial cell division site-determining factor MinD mediates placement of the chloroplast division apparatus," *Research Paper, Current Biology* 10:507-516 (2000).
Wakasugi et al., "Complete nucleotide sequence of the chloroplast genome from the green alga *Chlorella vulgaris*: The existence of genes possibly involved in chloroplast division," *Proc. Natl. Acad. Sci. USA* 94:5967-5972 (1997).

* cited by examiner

*Primary Examiner*—Anne Kubelik
(74) *Attorney, Agent, or Firm*—Quarles & Brady LLP

(57) ABSTRACT

Disclosed are MinD protein coding sequences that play a critical role in regulating the division of plastids in plants. Also disclosed is a method for obtaining transgenic plants with novel phenotypes, characterized by alterations in plastid shape, number and/or size.

25 Claims, 3 Drawing Sheets

```
Pw  MNKLHYFINNIFNLIVYYLYSLYFKEDKIKRRLSNMTKKQENYNKEQLIKEKP
At                                       MASLRLFSTNHQSLLLPS

Sy                                        MN-RIIVVTSGKGGVG
Gt                                        MA-RIVVITSGKGGVG
Cv                 MVFSTGNGDDNSKG----LE-RVIVITSGKGGVG
Pw  EERKIIKEQLEQLIQKPSESEYNTELDIELDKGDSDELEPRVIVITSGKGGVG
No                            MTMQDKEPSAPAC-RVIVITSGKGGVG
At  SLSQKTLISSPRFVNNPSRRSPIRSVLQFNRKPELAGETPRIVVITSGKGGVG
Os     MAFAPRLLLPSRCPPPASSPARHGGRTAPELSGPTPRVVVVTSGKGGVG
                                              *******

Sy  KTTTTANLGAALARLGKKVVLIDADFGLRNLDLLLGLEQRIVYAIDVLADEC
Gt  KTTVTANLGMALAQLGYRTALIDADIGLRNLDLLLGLENRVIYALEVLSGEC
Cv  KTTTTANLGMSIARLGYRVALIDADIGLRNLDLLLGLENRVLYAMDIVEGQC
Pw  KTTTTANLGMSIARPGYRVALIDADIGLRNLDLLLGLENRITFAMDIIEGRC
No  KTTATANLGMCIARLGYRVALIDADIGLRNLDLLLGLENRVVYAMEVIEGQC
At  KTTTTANVGLSLARYGPSVVAIDADLGLRNLDLLLGLENRVNYTCVEVINGDC
Os  KTTTTANLAASLARLSLSAVAVDADAGLRNLDLLLGLENRVHLTAADVLAGDC
     *  *    *    *     * * ******    *  *

Sy  TIDRALVKDKRLPNLVLLPAAQNRSKD--AINAEQMQSLVEQLKD----KFDY
Gt  RLEQALIKDKRQPNLVLLPAAQNRNKD--SVTEEQMKFLVNLLVN----DYDY
Cv  RLDQALIRDKRWKNLALLAISKNRQKY--NVTRKNMQNLIDSVKEL---GFQF
Pw  RLDQALVREKRWKNLALLAVSKNHQKY--NVTQQHMRQLVFSIKEL---GINS
No  RLEQALIRDKRWKNLSMLAMSKNRQRY--NMTRKNMMMIVDSIKER---GYQY
At  RLDQALVRDKRWSNFELLCISKPRSKLPMGFGGKALEWLVDALKTRPEGSPDF
Os  RLDQALVRHRALHDLQLLCLSKPRSKLPLAFGSKTLTWVADALRRAAN-PPAF
      **

Sy  IIIDCPAGIEAGFRNAVAPAQEAIIVTTPEMSAVRDADRVIGLLEAEDIGKIS
Gt  LLIDCPAGIETGFHNAIGPAQEAIVVTTPEIAAVRDADRVIGLLEANGIKQIK
Cv  VLIDCPAGIDVGFINAIASAQEAVIVTTPEITAIRDADRVAGLLEANGIYNVK
Pw  ILIDCPAGIDVGFINAIAPAQEAIIVTTPEITAIRDADRVAGLLEANTIVDTK
No  ILIDCPAGIDAGFVNAIAPADEAILVTTPEITAIRDADRVAGLLEANDFYNVR
At  IIIDCPAGIDAGFITAITPANEAVLVTTPDITALRDADRVTGLLECDGIRDIK
Os  ILIDCPAG*   *   *   *   *     **  **   *
     * ***

Sy  LIVNRLRPETVQLNQEISVEDILDLLAVPLIGILPDDQKIIISTNKGEPLVME
Gt  LLVNRLRPQHVKANDHMSVADVREILAIPLIGVIPEDECVIVSTNRGEPLVLE
Cv  LLVNRVRPDEIQKNDIMSVRDVQEMLGIPLLGAIPEDTSVIISTNKGEPLVLN
Pw  LLLNRVRMDEIQNSTDLSIMDVQETLGIPLLGAIPEDTNVIISTNRGEPLVLD
No  LVANRVRPEEIQQNDDMSVDVQGMIGVPLLGAIPEDKNVIISTNRGEPLVCQ
At  MIVNRVRTDEIKGEDIMSVLDVQEMLGLSLLGVIPEDSEVIRSTNRGEPLVLN
         *                  *              *   ***

Sy  EKLSVPGIAFQNIARRLEGQDIPFLDFMAAHNTLLNRIRRRLLGG---
Gt  KNLSLPGIAFEHTACRLDGQEIEFLDLQSYSRGPLKRLRRPFLGSSTN
Cv  KKLTLSGIAFENAARRLIGKQDYFIDLTSPQKGMFQKLQEPFLGEE--
Pw  KKLTLSGIAFENAARRLIGKEDYFVDLDIPTKSIIKKIQKFFWGEF--
No  KTITLAGVAFEEAARRLVGLPS--PSDSAPSRGWFAAIRRLWS-----
At  KPPTLAGIAFEQAAWRLVEQDS-MKAVMVEEEPKKRGFFSFFGG----
         *      *
```

FIG 1

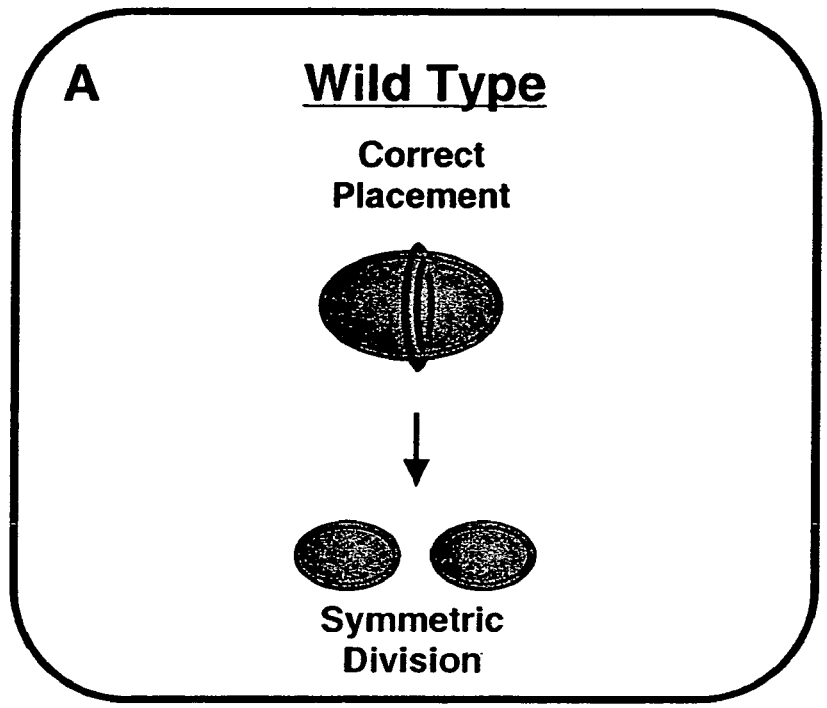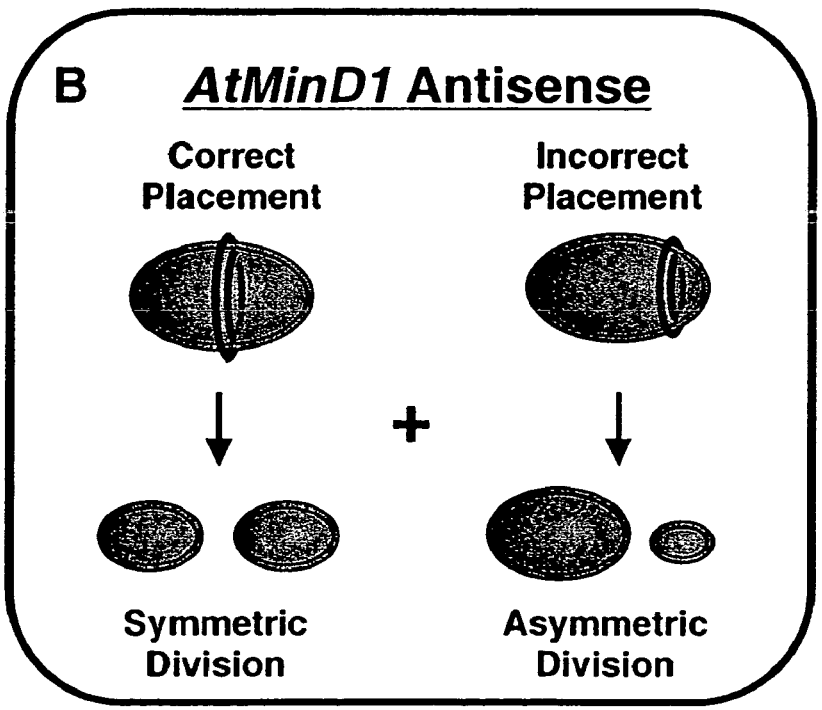
FIG 2

MANIPULATION OF A MIND GENE IN PLANTS TO ALTER PLASTID SIZE, SHAPE AND/OR NUMBER

CROSS-REFERENCE TO RELATED APPLICATIONS

This application claims priority from provisional patent application Ser. No. 60/130,403 filed Apr. 19, 1999.

STATEMENT REGARDING FEDERALLY SPONSORED RESEARCH OR DEVELOPMENT

Not applicable.

BACKGROUND OF THE INVENTION

The modern agricultural industry has devoted considerable resources toward the development of phenotypically distinct plants with economically advantageous qualities. Valuable features in food crops include increased vigor, disease resistance, greater yields, extended shelf-life, and enhanced nutritional content.

The development of high yielding food crops is particularly important. Each year, the tillable land available for agricultural production is reduced as more acreage is devoted to alternative uses. At the same time, the human population is rapidly increasing. Therefore, it is essential to increase agricultural productivity in order to meet the nutritional needs of the world's burgeoning population.

Efforts to develop crop plants that produce higher yields have been directed toward pest control, or toward the selection and breeding of varieties that bear greater numbers of fruit, or that produce larger fruit. These crop breeding endeavors are very time-consuming and labor-intensive, but have historically increased crop yields incrementally over time. Modern techniques of recombinant DNA manipulation and genetic engineering offer the prospect of the more rapid creation of new plant varieties with novel traits. The creation of genetically modified, or transgenic, plants with altered phenotypes arising from artificially inserted genetic constructions has become a common practice in modern agriculture.

If one is going to genetically engineer plants, the genetic engineering or recombinant DNA manipulation of plastids is one area in which improvements to plants might be targeted. Plastids are membrane-delimited organelles in plant cells which are essential for sustaining plant growth and cell viability. They are the site for the synthesis of essential amino acids, vitamin E, pro-vitamin A, starch, certain growth hormones, lipids, and pigments such as carotenes, xanthophylls, and chlorophylls. In plants, plastids include chloroplasts, chromoplasts, leucoplasts and amyloplasts, which are typically found in all organs of the plant including its leaves, roots, stems, petals, and seeds.

The specialized plastid chloroplast is where photosynthesis occurs. Photosynthesis in plants is an important biosynthetic process upon which virtually all living organisms depend for our very existence. During photosynthesis, energy in the form of light is converted to ATP, which fuels a series of enzymatic reactions that catalyze the synthesis of carbohydrates, which are further used for metabolic energy in the plant. Photosynthesis also produces molecular oxygen ($O_2$) is a byproduct. Because photosynthesis is the source of metabolic energy in plants, photosynthetic efficiency is a significant factor associated with general plant growth and vigor. Chloroplasts also synthesize amino acids and lipids.

U.S. Pat. No. 5,981,836, incorporated herein by reference, discloses genetic constructs capable of altering the number and size of plastids in plant cells. These construct contain an *Arabidopsis* plastid division FtsZ protein coding sequence and a promoter, not natively found associated with the FtsZ protein coding sequence, which promotes expression of the *Arabidopsis* plastid division FtsZ protein coding sequence in the plant. The FtsZ protein is a bacterial cytoskeletal protein and structural homologue of tubulin that polymerizes on the inner surface of the cytoplasmic membrane to forms a cytokinetic ring during cell division. Transgenic expression of the coding sequence results in a high percentage of novel phenotypes characterized by alterations in the number and size of plastids in the cells of the plant in which the construct is expressed.

There is also on-going efforts to make transgenic plants that are more suited for particular applications or which have transgenes inserted into them to have localized effects inside the cells of the plants. For example, there are a number of transgenes inserted into plants which maximize the usefulness of the inserted traits if the transgenes are transformed into the chloroplasts of the plant. Since one method for chloroplast transformation is based on the delivery of transgenes coated onto small carrier particles into the interior of the chloroplasts themselves, this technique is easier to perform if the chloroplasts themselves are larger than normal. So one technique that would be useful for this effort is to make plants with larger chloroplasts.

What is needed in the art are additional means for altering the shape, size and/or number of chloroplasts and other plastids in agronomically and horticulturally important plants to achieve greater plant productivity and nutritional quality.

BRIEF SUMMARY OF THE INVENTION

The present invention is a plant comprising in its genome a genetic construction including a sense or antisense MinD protein coding sequence and a promoter, not natively associated with the MinD protein coding sequence, which promotes expression of the sequences in the plant, wherein expression of the sequence in the plant causes alterations in the number, shape and/or size of the plastids in the plant cells of the plant. The present invention also discloses a method for altering the number, shape and/or size of the plastids using the genetic construct described above.

The present invention also includes DNA sequences (SEQ ID NO:1 and SEQ ID NO:3) representing genes that function in regulating plastid division, and which, when ectopically expressed, alters the number, shape and/or size of chloroplasts and other types of plastids present in plant cells.

The present invention is also directed toward a genetic construct including a MinD protein coding sequence and a promoter that promotes expression of the sequence in plants, the promoter not being natively associated with the MinD protein coding sequence.

The present invention is also a seed, including in its genome a genetic construct comprising a MinD protein coding sequence and a promoter, not natively associated with the MinD protein coding sequence, that promotes gene expression in plants.

The present invention is also a plant cell including in its genome a genetic construct comprising a MinD protein coding sequence and a promoter, not natively associated with the MinD protein coding sequence, that promotes gene expression in plants.

It is an object of the present invention to provide a transgenic plant that has a novel phenotype with advantageous qualities, including decreased numbers of enlarged chloroplasts.

Other objects, advantages, and features of the present invention will become apparent after review of the specification and drawings.

BRIEF DESCRIPTION OF THE SEVERAL VIEWS OF THE DRAWINGS

FIG. 1 is an illustration of the alignment of MinD proteins from several photosynthetic organisms (including SEQ ID NO:2 (AT) (*Arabidoipis*), SEQ ID NO:7 (Pw)(*Prototheca*), SEQ ID NO:8 (Sy)(*Synechocystis*), SEQ ID NO:9 (Gt) (*Guillardia*), SEQ ID NO:10 (Cv) (*Chlorella*), SEQ ID NO:11 (No)(*Nephroselmis*) and SEQ ID NO:12 (Os)(*Oryza*) (partial)).

FIG. 2 is a model showing the proposed effect of plastid-localized AtMinD1 on the positioning of the plastid division apparatus.

DETAILED DESCRIPTION OF THE INVENTION

Figure 3:
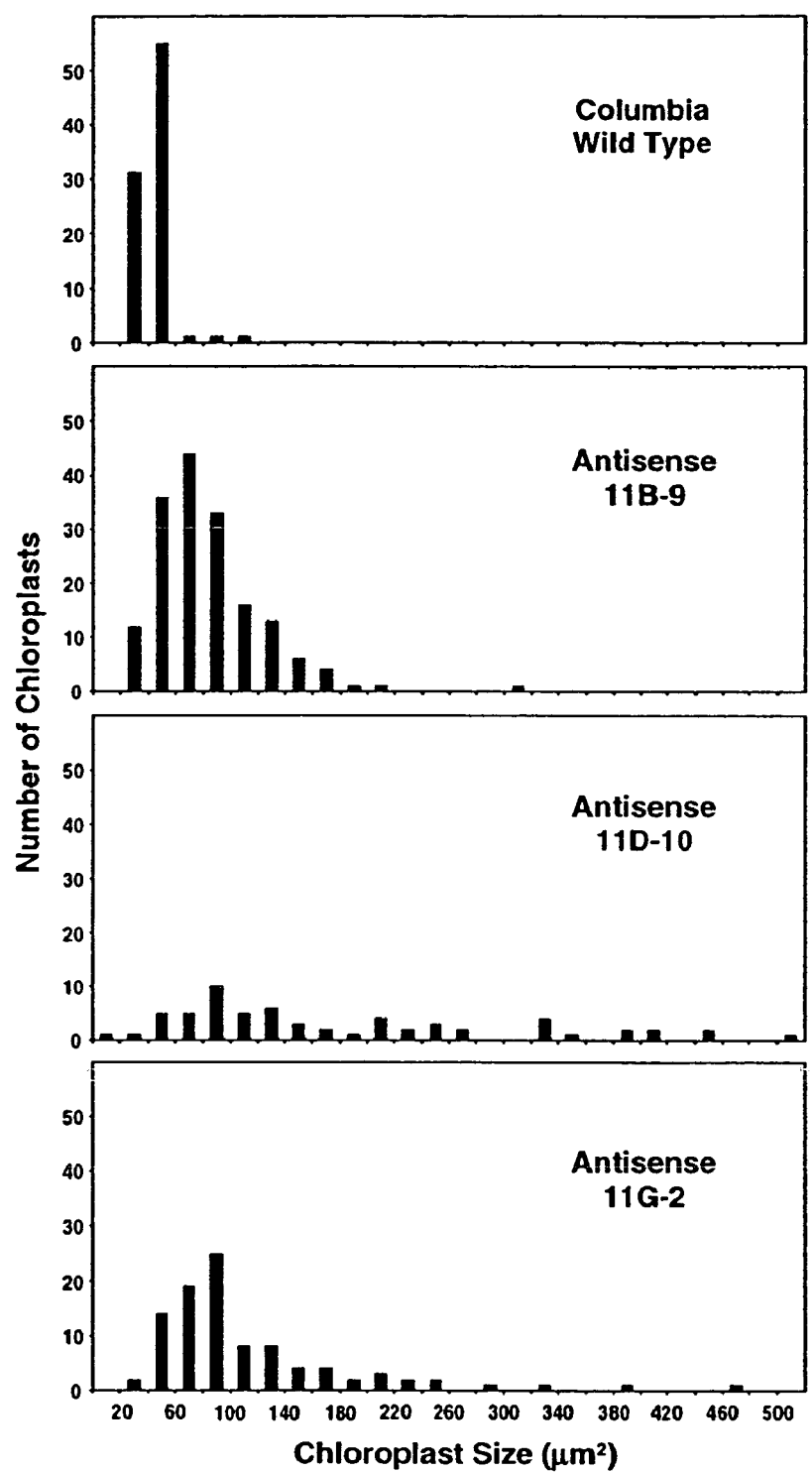
FIG. 3 are graphs illustrating the frequency distribution of chloroplast sizes in mesophyll cells from *Arabidopsis* wild-type plants and *Arabidopsis* plants transformed by an antisense AtMinD1 construct.

It is disclosed here that nuclear-encoded, plastid-targeted forms of genes encoding a MinD protein have been identified in plants, and these genes have been shown to play an important role in the division of plastids. The MinD genes had previously only been demonstrated to exist in prokaryotes. The data presented here demonstrates that all plants natively have MinD genes, and that the function of the endogenous genes can be altered by genetic engineering. Reduced expression of an endogenous MinD gene in a transgenic plant results in asymmetric plastid division leading to an abnormally heterogeneous distribution of plastid numbers and sizes in plant cells. Overexpression of the MinD gene in a transgenic plant results in the inhibition of plastid division and fewer numbers of large plastids.

One aspect of the present invention is a plant that contains in its genome a genetic construct having a sense or antisense plant MinD protein coding sequence and a promoter, not natively associated with the MinD protein coding sequence, which promotes expression of the sequence in plant cells. Insertion of the genetic construction results in plants having a high percentage of novel phenotypes characterized by alterations in the number, shape and/or size of plastids in cells of the plant in which the construct is expressed.

The identification and characterization of two initial MinD coding sequences from plants that are useful in the present invention are described in the examples below. The sequence designated AtMinD (At for *Arabidopsis Thaliana*, SEQ ID NO:1) was identified by BLAST similarity searching on the basis of homology to bacterial MinD genes. The sequence designated TeMinD (Te for *Tagetes erecta*, SEQ ID NO:3) was identified by cDNA library screening on the basis of homology to bacterial MinD genes.

It should be understood that the initial plant MinD genes, the identification of which are described here, were identified based on sequence comparison with the analogous genes known in bacteria. Since the bacterial gene sequence was sufficient to permit the identification of plant MinD genes, and since the plant MinD will be more closely related to each other than they are to bacterial genes, the data presented here make possible the recovery of the respective MinD gene from most, if not all, plant species.

Based on analogous function to the bacterial proteins, plant MinD proteins are involved in the placement of the FtsZ ring during plastid division. The plant MinD genes are believed to descend from a key prokaryotic cell division mechanism through the evolution of photosynthetic eukaryotes. The process of cell division in bacteria is mediated by a set of at least ten proteins that assemble into a macromolecular complex at the cell midpoint. Chief among these is the bacterial cell division protein FtsZ, a prokaryotic cytoskeletal protein and structural homologue of tubulin that polymerizes on the inner surface of the cytoplasmic membrane to forms a contractile ring. Assembly of the FtsZ ring is the earliest known step in formation of the bacterial division complex.

The mechanism by which placement of the FtsZ ring is determined in bacteria is still uncertain, but genetic studies have uncovered some of the critical players. In *E. Coli*, precise localization of the FtsZ ring at the cell center is established by the Min system of proteins, comprising MinC, MinD, and MinE. In mutants lacking MinC or MinD, the FtsZ ring is frequently misplaced near one of the cell poles such that cell division results in the formation of nonviable "minicells" which lack chromosomes and cannot expand. Thus, MinC and MinD act in wild type cells by inhibiting FtsZ ring formation at polar sites and restricting the ring to the midcell. This activity in *E. coli* involves an oscillation of both MinC and MinD from one cell pole to the other. MinE, which is targeted independently of FtsZ to a medial ring, prevents MinC and MinD from localizing at the midcell, thereby allowing the FtsZ ring to assemble specifically at this position.

In *Bacillus subtilis*, MinC and MinD also prevent FtsZ ring assembly at polar sites, but are localized at both poles simultaneously and do not oscillate. *B. subtilis* lacks MinE, relying instead on a different protein, DivVIA, to tether MinC and MinD to the cell poles. Though the mechanisms restricting the activity of MinC and MinD to polar sites are different in *E. coli* and *B. subtilis*, in both cases the absence of these proteins at the midcell establishes the site of FtsZ ring assembly, and MinD is required for the proper localization and division-inhibiting activity of MinC.

In plants and other photosynthetic eukaryotes, constriction of the chloroplast during division usually occurs at the middle of the plastid perpendicular to the long axis. See the diagram of FIG. 2. These observations indicate that the positioning of the plastid division machinery in plants, like the positioning of the FtsZ ring in bacteria, is a carefully regulated process. The discovery of the existence of a nuclear gene from *Arabidopsis* and *Tagetes* encoding a chloroplast-targeted homologue of MinD and the examination of the relationship between chloroplast shape, size and number in transgenic plants indicates that a Min-based system operates in specifying placement of the plastid division components in plant cells during plastid division.

As used herein, "MinD" refers to the *Arabidopsis* MinD protein coding sequence (SEQ ID NO:2) and the *Tagetes erecta* (Marigold) MinD protein coding sequence (SEQ ID NO:4), as well as the analogous gene sequences from other plants as well as variations and mutants thereof which retain plastid division control functionality. As shown in FIG. 1, the MinD proteins are highly conserved among diverse species capable of conducting photosynthesis. It is expected that all plants contain MinD genes homologous to the *Arabidopsis* and *Tagetes* genes. The bacterial MinD protein is also homologous to the plant MinD genes and can be used as well in transgenic plants. Given the apparent ubiquitousness and high degree of conservation of the MinD proteins among plant species, it is reasonable to expect that MinD genes, of which the AtMinD and the TeMinD genes are but two examples, from any plant could be used in the practice of the present invention. For example, MinD genes from plants that are raised for their agricultural or horticultural value may be used in the practice of the present invention. It can be expected, from the sequence data presented below, that any plant MinD have at least 50%, and more likely at least 80%, sequence identity at the amino acid level with either the *Arabidopsis* or the *Tagetes* MinD protein sequence. The *Arabidopsis* and *Tagetes* MinD sequences compared to each other have a sequence identity at the amino acid level of 92%, a high degree of sequence identity. By sequence identity it is meant that at least the defined percentage of amino acid residues in the proteins being compared have the same identity and are located in the same sequence order as the corresponding amino acids in the protein to which it is being compared. A useful calculation (as used here) for amino acid sequence identity comparison is done using pairwise comparisons using the SIM local alignment algorithm (Huang and Miller (1991)) with the default parameters specified on the ExPASy Molecular Biology Server, Swiss Institute of BioInformatics. The comparison at the amino acid level means that two genes being compared may have nucleotide sequences that differ more greatly than the amino acid sequence, which is possible given the degeneracy of the genetic code, but that they encode amino acids which have the requisite degree of sequence identity.

It is specifically contemplated that any MinD protein coding sequence could be used in the practice of the present invention. "MinD protein coding sequence" is defined to include any plant DNA sequence capable of overexpressing or reducing the activity of the MinD gene native to the plant in which the MinD protein coding sequence is introduced. A MinD protein coding sequence may be an unmodified genomic entire gene sequence isolated from any plant, a cDNA sequence derived from any plant, a genomic or cDNA sequence that is modified to contain minor nucleotide additions, deletions, or substitutions, or a synthetic DNA sequence. The term is intended to apply, as well, to analogous sequences from other plants as well as allelic variations and mutations which are still capable of controlling plastid division.

By "plastid division activity" it is meant the ability to cause alterations in the number or size of the chloroplast or other types of plastids present in cells of a transgenic plant in which the MinD protein coding sequence is expressed.

By "transgene" it is meant to describe an artificial genetic construction carried in the genome of a plant and inserted in the plant or its ancestor by gene transfer. Such transgenes are transmissible by normal Mendelian inheritance once inserted into the genome of a parental plant.

It is specifically envisioned that transgenic plants can be made with a transgene for a MinD protein coding sequence which selectively either up-regulates or down-regulates plastid MinD division activity. For fewer plastid divisions, extra copies or high expression copies of MinD protein coding sequence transgenes are inserted into plants, resulting in fewer and larger plastis in the transgenic plants. Sometimes high expressing plants will produce only one or a very fewer chloroplasts per cell. For more plastid division activity, the use of an antisense MinD protein coding sequence transgene, or any other gene inhibition technique, may be used to down regulate plastid division activity resulting in a greater variability in plastid number and size. Both up and down regulation of plastids will be useful for certain applications.

Transgenic *Arabidopsis* plants were obtained as a model system using the *Agrobacterium* transformation system, as described in the examples. *Arabidopsis* is often used as a model plants in such experiments because of the relatively small size of its genome and also because it is a small compact plant easy to grow and easy to conduct experiments on. *Agrobacterium*-mediated transformation is used since it is known to work well with many dicot plants and some monocots. Other methods of transformation equally useful in dicots and monocots may also be used in the practice of the present invention. Transgenic plants may be obtained by particle bombardment, electroporation, or by any other method of transforming plants known to one skilled in the art of plant molecular biology. The experience to date in the technology of plant genetic engineering is that the method of gene introduction is not of particular importance in the phenotype achieved in the transgenic plant.

The present invention is also directed toward a genetic construct comprising a MinD protein coding sequence and a promoter, not natively associated with the sequence, which promotes expression of the MinD protein coding sequence in plants at levels sufficient to cause novel phenotypes. The construct may contain the sequence in either the sense or antisense orientation. The development of constructs that have been found to alter the number or size of chloroplasts in transformed plant cells is described in the examples below. Briefly, relevant features of these constructs include a kanamycin resistance marker and, in 5' to 3' order, the CamV 35S promoter operably connected to a chloroplast division sequence, and a transcriptional terminator, or polyadenylation sequence, from an *Agrobacterium* gene known as OCS.

The CaMV 35S promoter is a constitutive promoter known to function in a wide variety of plants. Other promoters that are functional in the plant into which the construct will be introduced may be used to create genetic constructs to be used in the practice of the present invention. These may include other constitutive promoters, tissue-specific promoters, developmental stage-specific promoters, and inducible promoters. Promoters may also contain certain enhancer sequence elements that improve the efficiency of transcription.

The examples below describe the use of an expression vector that contains a kanamycin resistance gene as a selectable marker for selection of plants that have been transformed with the genetic construct. Numerous selectable markers, including antibiotic and herbicide resistance genes, are known in the art of plant molecular biology and may be used to construct expression vectors suitable for the practice of the present invention. Expression vectors may be engineered to include screenable markers, such as beta glucuronidase (GUS).

The genetic constructs employed in the examples below were engineered using the plasmid vector pART27 (Gleave, *Plant Mol. Biol.* 20:1203–1207, 1992). It is anticipated that other plasmid vectors or viral vectors, or other vectors that are known in the art of molecular biology, will be useful in the development of a construct that may be used to transform a plant to obtain expression of a MinD protein coding sequence. The creation of a genetic construct suitable for transformation using the *Agrobacterium* system is described, however, any transformation system for obtaining transgenic plants may be used. The construction of a vector and the adaptation of that vector to a particular transformation system are both within the ability of one skilled in the art.

The present invention also contemplates a method for altering the shape, size and/or number of plastids in a plant, relative to the wild type plant. The method comprises the steps of making a genetic construct comprising a MinD protein coding sequence and a promoter, not be natively associated with the sequence, transforming the plant with the genetic construct, and growing the transgenic plant so created as to allow expression of the genetic construct. The genetic construct as a transgene in the plant will change the size, shape and/or number of the plastids in the plant cells of the plant.

Alterations in plastid size, shape and/or number via genetic engineering of MinD expression in accordance with the present invention has the potential to result in improved productivity or increased vigor due to enhanced photosynthetic capacity and allow enhanced production of commercially important compounds that accumulate naturally or as a result of genetic engineering. The ability to alter the expression of the chloroplast division genes allows the manipulation of the size and number of chloroplasts in plant cells. Because chloroplast number is known to have a direct effect on photosynthetic capacity, it is likely that by manipulating levels of plastid division proteins in genetically engineered plants to achieve increased numbers or size of plastids, one may obtain plants having advantageous properties.

In the examples below, changes in chloroplast numbers and size were examined in plants in which a MinD protein coding sequence was expressed as a transgene in transgenic plants. It is expected that MinD protein coding sequences are also involved in regulating the division of other plastids, including chromoplasts, amyloplasts, and leucoplasts. These plastids are of great agronomic importance because they synthesize carotenoids, starch, and oils. Manipulation of the expression of chloroplast division sequences to alter the number or size of plastids other than chloroplasts is within the scope and spirit of the present invention.

FIG. 2 sets forth a model for the structural organization of the plastid division apparatus in plants in which plastid division is mediated by two FtsZ-containing plastid-dividing rings, one localized on the stromal surface of the inner chloroplast envelope membrane containing FtsZ 1, and the other on the cytosolic surface of the outer envelope membrane containing FtsZ2 (FIG. 2, Panel A). Implied in this model is the coordinated positioning of division components across the envelope at the plastid midpoint. In wild-type plants, both stromal and cytosolic PD rings, proposed to contain FtsZ1 and FtsZ2, respectively, are localized at the plastid midpoint, and the coordinated constriction of the two rings results in symmetric division yielding two daughter plastids approximately equal in size (FIG. 2, panel A). Antisense repression of MinD leads to misplacement of the stromal FtsZ1 ring in many, though not necessarily all, plastids. When it does occur, the cytosolic FtsZ2 ring in turn becomes localized to a site on the outer membrane corresponding to the site of misplacement of the FtsZ1 ring (FIG. 2, panel B, right). Other components of the two PD rings presumably also assemble at this position. The coordinated action of the two mislocalized PD rings results in a productive but asymmetric division event, yielding daughter plastids of unequal size. Multiple rounds of plastid division in which the stromal FtsZ1 ring was sometimes but not always misplaced could further increase the size variability.

The nonlimiting examples that follow are intended to be purely illustrative.

EXAMPLES

Isolation And Characterization Of A Mind Gene In *Arabidopsis Thaliana*.

An homolog of the bacterial MinD gene was isolated from *Arabidopsis thaliana* as follows. The amino acid sequence of *Chlorella vulgaris* MinD was used as a query sequence to search the nonredundant GenBank database using the TBLASTN algorithm. A highly significant match was found to an open reading frame in the P1 library clone MZF18 (accession number AB009056) from chromosome V of *Arabidopsis*. This *Arabidopsis* DNA sequence, designated AtMinD1, is shown in SEQ ID NO:1. It contains an open reading frame (ORF) spanning nucleotides 32,980 through 33,957 on the minus strand of MZF18, which is uninterrupted by introns and encodes a polypeptide of 326 amino acids with a calculated molecular weight of 35,690. This *Arabidopsis* MinD amino acid sequence, designated AtMinD, is shown in SEQ ID NO:2.

FIG. 1 illustrates a sequence comparison by sequence alignment between the sequence from *Arabidopsis* and the corresponding gene sequences from other photosynthetic organisms. The sequences used in the alignment are identified as follows: Sy, *Synechocystis* PCC6803, Q55900; Gt, *Guillardia theta* (plastid genome), AAC35621; Cv, *Chlorella vulgaris* (plastid genome), P56346; Pw, *Prototheca wickerhamii* (plastid genome), CAB53105; No, *Nephroselmis olivacea* (plastid genome), AAD54908; At, *Arabidopsis thaliana*, AB009056 (translated sequence of nucleotides 32,980 through 33,957, minus strand); Os, *Oryza sativa* AF149810 (partial sequence). Only the first 163 amino acids of the *O. sativa* sequence were used in the alignment. Dashes (-) indicate gaps in the alignment. Gaps at the amino termini were removed manually. Identical amino acids among the sequences shown are boxed in black. Asterisks (*) indicate residues identical among all proteins when the following bacterial MinD sequences are added to the alignment (not shown): *Bacillus subtilis*, Q01464; *Escherichia coli*, BAA36022; *Helicobacter pylori* 26695, AAD07400; *Deinococcus radiodurans*, AAF10331; *Aquifex aeolicus*, AAC06996.

This alignment of several MinD amino acid sequences in FIG. 1 from various photosynthetic organisms was performed using CLUSTAL W 1.8. The alignment revealed regions of high sequence similarity, indicating that the gene has been highly conserved during the evolution of chloroplasts. The MinD protein encoded by AtMinD1 shares a 65% identity with the MinD protein from *Chlorella vulgaris* (P56346), a slightly lower extent of identity (58–62%) with the MinD proteins encoded in the plastid genomes of *Guillardia theta* (AAC35621), *Prototheca wickerhamii* (CAB53105), *Nephroselmis olivacea* (AAD54908) and *Oryza sativa* (AF149810), and a 53% identity with the MinD protein from the photosynthetic prokaryote *Synechocystis* (PCC6803, Q55900). AtMinD also shares a greater than 40% amino acid identity with the bacterial MinD sequences of *Bacillus subtilis* (Q01464); *Escherichia coli* (BAA36022); *Helicobacter pylori* 26695 (AAD07400); *Deinococcus radiodurans* (AAF10331); and *Aquifex aeolicus* (AAC06996), data not shown. Sequence identity was calculated using the SIM local alignment algorithm. (Huang and Miller 1991) with the default parameters specified on the ExPASy Molecular Biology Server, Swiss Institute of BioInformatics.

Isolation And Characterization Of A Mind Gene In *Tagetes Erecta* (Marigold).

An homolog of the bacterial MinD gene was isolated from *Tagetes erecta* (Marigold) as follows. Color complementation was used to screen a cDNA library made from poly A RNA isolated from stage 3 and 4 petals (approximately 8–10 mm and 13–15 mm in length, respectively) taken from the marigold variety Dark Orange Lady (W. Atlee Burpee Company, Clinton, Iowa). This technique relies on the ability of an *E. coli* engineered to express certain carotenoids to accumulate the carotenoids when carotenoid biosynthetic genes are expressed from a plasmid. A second plasmid from a library of interest can be introduced into this background with a different selectable marker and a compatible replicon which enables the selection of colonies having a desired phenotype. This color complementation method has proven to be effective for isolating carotenoid biosynthetic genes from a number of organisms.

To construct the cDNA library, total RNA from the marigold petals was isolated by LiCl precipitation and poly A RNA was obtained by two passes of the RNA over an oligo dT cellulose column. (Stratagene, La Jolla, Calif.). Single clone excision and mass excision of the lambda library to yield phagemids were then performed as recommended by the manufacturer. Isolated plasmids were sequenced by primer walking on both strands using a dRhodamin cycle sequencing kit.

*E. coli* cells (strain DH5α) containing the plasmid pAC-ZEAX for producing zeaxanthin were transformed with plasmids containing cDNA from the Marigold library, and then grown in LB supplemented with chloramphenicaol to maintain the carotenoid-gene containing plasmid and with ampicillin (100 μg/ml) to maintain the marigold library plasmids.

A low temperature screen led to the isolation of a marigold gene encoding the plastid division protein MinD. This screen was based on the observation that *E. coli* genetically engineered to accumulate zeaxanthin grew more slowly at 18° C. than *E. coli* harboring the vector plasmid alone and accumulated significantly less zeaxanthin than when grown at 37° C. The basis of this temperature dependent phenotype is unknown. When the marigold cDNA library was transformed into zeaxanthin containing *E. coli*, numerous rapidly growing, highly pigmented colonies were identified in a background of pale, slow growing colonies. Plasmids isolated from several of these colonies were sequenced and similarity searches against the publicly available databases revealed a marigold gene with similarity to the *E. coli* MinD protein. This *Tagetes* DNA sequence, designated TeMinD, is shown in SEQ ID NO:3 and its deduced amino acid sequence, designated TeMinD, is shown in SEQ ID NO:4.

Construction of Chimeric Sense and Antisense MinD Protein Coding Sequences.

The MZF18 clone (AB009056) was obtained from the *Arabidopsis* Biological Research Center in Columbus, Ohio. The region corresponding to the AtminD1 ORF was amplified from MZF18 with Deep Vent Polymerase (New England BioLab) using the following primers: forward primer, 5'-CCGAATTCGAAGCAGCAGCACTAT-CAATGG-3' (SEQ ID NO:5); reverse primer 5'-CGGAAT-TCGATCCGTTTGCCATTTAGCC-3' (SEQ ID NO:6). Both primers incorporated recognition sites for EcoRI. The PCR product was sequenced in its entirety to ensure that no mutations had been introduced, and ligated in both orientations into pBluescript (Stratagene). The plasmid with the 5' end of the insert nearest the T3 promoter was designated KG405; the plasmid with 5' end of the insert nearest the T7 promoter was designated KG406. The plasmids were maintained in a minCDE deletion strain of *E. coli*, RC3F. For the transgenic constructs, the EcoRI-restricted PCR fragment was ligated into the EcoRI cloning site of pART7 behind the CaMV 35S promoter in either the sense or antisense orientation. The transgenes were then excised from the resulting plasmids with NotI and ligated into the NotI cloning site in the binary transformation vector pART27, yielding plasmids KG402 containing the AtMinD1 antisense construct, and KG404 containing the AtMinD1 sense construct. Both transformation vectors also included a selectable marker from pART27 conferring plant resistance to kanamycin.

Characterization of MinD Synthesis in Plants.

Relative to the MinD proteins from *C. vulgaris* and several prokaryotes, AtMinD contains an amino terminal extension with features common to chloroplast transit peptides. These include alanine as the second residue, a relatively high proportion of hydroxylated amino acids, and few acidic residues. An in vitro chloroplast import assay was performed to determine whether this extension was able to function as a chloroplast targeting sequence.

Plasmid KG405, described above, was linearized with BamHI and transcribed using T3 RNA polymerase. A plasmid containing the prSS control encoding the small subunit of pea RuBP carboxylase was linearized with PstI and transcribed with SP6 RNA polymerase. The resulting transcripts were translated in a rabbit reticulocyte lysate translation system (Promega) containing [$^{35}$S]methionine (DuPont/NEN). Import reactions were carried out using chloroplasts isolated from 8- to 12-day-old pea seedlings (*Pisum sativum* var. Little Marvel, Olds Seed Company, Madison, Wis.) and purified over a Percoll gradient. Intact chloroplasts were reisolated and resuspended in import buffer (330 mM sorbitol, 50 mM Hepes/KOH, pH 8.0) at a concentration of 1 mg chlorophyll/ml. Thermolysin treatment of import products was performed and import products were analyzed by SDS-PAGE and fluorography.

The in vitro transcription of the AtMinD1 ORF, followed by the in vitro translation of the resulting transcript in the presence of [$^{35}$S]methionine, yielded a full-length, radiolabeled translation product that migrated at 39.7 kD, somewhat above its calculated mass. When added to the isolated pea chloroplasts, the translation product was processed to a smaller form migrating at 35.6 kD. The processed form of the protein was soluble following import, and was fully protected from a post-import treatment with the protease thermolysin. In a control set of reactions, the small subunit of pea RuBP carboxylase/oxygenase, a soluble stromal protein, behaved identically. These results provide strong evidence that AtMinD, like the *Arabidopsis* FtsZ1, is synthesized as a precursor on cytosolic ribosomes and post-translationally targeted to the chloroplast where it is processed to a mature form.

Effect of Antisense Repression of MinD on Chloroplast Size and Number.

To demonstrate that the AtMinD1 gene functions in the placement of the plastid-localized FtsZ ring and the positioning of the plastid division machinery, the transformation vector KG402, containing the AtMinD1 antisense construct, was introduced into *Arabidopsis* plants (ecotype Columbia (Col-0)) by *Agrobacterium*-mediated transformation.

The *Arabidopsis* plants utilized arose from seeds sown on a Supersoil potting mix and vermiculite in a ratio of 3:1. The seeds were incubated at 4° C. in the dark for two days before being moved to growth chambers and grown at 22° C. with 16 hrs of daylight. The age of the plants was calculated from the first day of their transfer to growth chambers.

*Agrobacterium*-mediated transformation was performed by a freeze-thaw method using *Agrobacterium tumefaciens* C58 (GV3101). The plasmids were checked for rearrangements following transfer to *Agrobacterium* by back-transformation to *E. coli* and restriction analysis. The transformation vectors were introduced into the *Arabidopsis* plants using the floral dip procedure. Transformants were selected by germination in nutrient medium containing 50 or 100 mg/l kanamycin and transplanted to soil 7–10 d after germination for propagation and analysis. Kanamycin resistant (kan$^r$) plants that originated from different pots were assumed to be derived from independent T-DNA insertion events for the purposes of phenotype characterization.

$T_1$ seeds were harvested from the inoculated plants, and transformants were selected on the basis of their resistance to the antibiotic. Leaf tissue from kan$^r$ plants were examined microscopically for effects on chloroplast size and number. Plants from 19 different pots were analyzed, ensuring that the phenotypes observed were the result of a minimum of 19 independent transformation events. Based on recent studies of T-DNA insertion patterns in *Arabidopsis* transformed by a similar procedure, it is likely that most of the kan$^r$ $T_1$ individuals, including those originating from the same pot, represented independent insertion events.

The phenotypes of the antisense transformants were initially investigated by examination of mesophyll cells from first leaves of 23-day-old $T_1$ plants. In wild-type plants, the leaves at this stage of development are fully expanded such that the cells have accumulated their full complement of approximately 100 chloroplasts, all of which fall within a narrow range of sizes (FIG. 3). Among the 164 kan$^r$ individuals examined from the 19 antisense transformations, 90 (55%) exhibited phenotypes that differed noticeably from wild type. Among these, 66 (73%) displayed a striking degree of heterogeneity in the sizes of the chloroplasts within a single mesophyll cell. This heterogeneity was evident both from visual inspection of the mesophyll cells under the microscope and from measurements of the frequency with which chloroplasts of different sizes were observed in the same cell (FIG. 3, panels B–D). The plastid size heterogeneity was even more pronounced in smaller cells from younger leaves in which chloroplasts are not yet fully expanded as they are in 23-day-old leaves.

Chloroplast numbers per unit cell area were also quite variable in the antisense plants, in contrast with wild type in which the number of chloroplasts per cell is tightly correlated with cell size. However, the chloroplasts were consistently fewer in number and larger in size than in wild type cells, suggesting a reduced number of plastid division events in most of the AtMinD1 antisense lines. The phenotypes observed in the $T_1$ generation were also observed in $T_2$ and $T_3$ progeny.

Although chloroplast numbers in cells from antisense plants were consistently lower and the chloroplast sizes far less uniform than in wild type, the linear relationship between the total chloroplast plan area and the total mesophyll cell plan area in the antisense lines was approximately the same as in wild type. This finding indicates that the reduced chloroplast numbers were compensated for by corresponding increases in chloroplast expansion so that total chloroplast volume was conserved. Similar results have been shown for other perturbations in chloroplast number and/or expansion.

A relatively small proportion (18%) of $T_1$ plants with visually detectable phenotypes under microscope displayed less heterogeneity in chloroplast size within single cells. Instead, the mesophyll tissue in these plants comprised a mixture of cells containing either wild-type numbers and sizes of chloroplasts or only a few large chloroplasts. Because the affected cells contained fewer chloroplasts than the number of proplastids present in leaf primordia, these observations suggest a significant inhibition of both proplastid and chloroplast division in some cells, but not in others.

Under the growth conditions used for the experiments, plants expressing the AtMinD1 antisense transgene grew more rapidly than wild type in the early stages of development (first leaves appeared earlier), but inflorescences appeared a few days later. This difference was evident through the $T_2$ and $T_3$ generations. In other aspects of growth and development, the antisense plants did not differ noticeably from wild type, however, careful measurements of growth parameters may reveal other subtle differences.

To confirm that the transgenic phenotypes resulted from reduced expression of the endogenous AtminD1 gene, a northern blot of poly(A)$^+$RNA isolated from antisense and wild type plants was probed with a radiolabeled RNA probe specific for AtMinD1. Total RNA was isolated from 23–27-day-old plants as described previously using 1 g of leaf tissue from independent transgenic lines ($T_3$) or from wild type to determine the expression levels of the AtMinD protein coding sequence. Only transgenic individuals exhibiting plastid size heterogeneity for the AtMinD1 antisense plants were used for RNA isolation. Poly(A)$^+$RNA was isolated with Oligotex resin (Qiagen) according to the manufacturer using total RNA as starting material, and quantified by measuring absorbance at 260 and 280 $\mu$m. Poly(A)$^+$RNA gel blots were prepared as described previously using nylon membrane (Micron Separations, Inc.). An RNA probe for hybridization specifically to sense AtMinD1 mRNA was prepared by linearizing KG406 with HindIII, and carrying out an in vitro transcription reaction in the presence of $^{32}$P-UTP (800 Ci/mmol; ICN, Costa Mesa, Calif.) as described previously, but using T7 RNA polymerase (New England BioLab). Blots were hybridized overnight and washed in 0.2×SSC (1×SSC is 0.15 M NaCl and 0.015 M sodium citrate) at 68° C.

The probe hybridized to two transcripts of about 1.1 and 1.7 kb, the smaller of which was more abundant. The probe remained bound to both transcripts when the blot was washed at very high stringency, indicating the two mRNAs were derived from either the same gene or from two closely related genes. Based on the size of the AtMinD1 open reading frame (978 bp), it was expected that AtMinD1 is represented by at least the smaller transcript. The levels of both transcripts were significantly reduced in the antisense plants when compared with wild type, indicating that the heterogeneity in chloroplast size and number in these plants was the result of reduced AtMinD1 expression.

To determine whether the heterogeneity in chloroplast size observed in the antisense repression of AtMinD1 could be the result of asymmetric chloroplast division, petal tissue from flowers of the transgenic plants were examined. Normally, in leaves of dicotyledonous plants, the division of chloroplasts is rapid and is not synchronized. Consequently, it can be difficult to observe chloroplasts in the process of division, particularly in the AtMinD1 antisense plants in which chloroplast numbers are reduced. However, in the present case, a high frequency of constricted plastids were documented in the *Arabidopsis* petals and easily viewed because the plastids were less densely packed than in mesophyll cells.

In many of the constricted plastids, the constriction was noticeably displaced from the center. This is in marked contrast from wild type plants in which petal plastids almost always appear to be constricted in the center. Asymmetric constriction of chloroplasts in leaf epidermal cells in the transgenic lines was also observed. Collectively, this data suggests that the chloroplast size variability in the AtMinD1 antisense plants results at least partially from asymmetric plastid division.

Effect of MinD Overexpression in Transgenic Plants.

To further analyze the role of AtMinD1 in plastid division, the transformation vector KG404, containing the sense AtminD1 construct under control of the CaMV 35S promoter, was introduced into *Arabidopsis* plants by *Agrobacterium*-mediated transformation as described above.

The phenotypes of 82 kan$^r$ T$_1$ individuals representing at least 13 independent transformation events were investigated microscopically. The predominant phenotype, observed in 52 (73%) of the 71 T$_1$ plants having phenotypes that were clearly distinguishable from wild type, was a dramatically reduced number of greatly enlarged chloroplasts in comparison to wild type. Cells in most of these plants appeared to contain five or fewer chloroplasts, and many had only a single large chloroplast. This phenotype contrasted with that observed in most of the antisense plants, in which the chloroplasts were generally more numerous, and indicates a more severe inhibition of plastid division. The phenotype was also inherited in the T$_2$ and T$_3$ progeny. Because the number of chloroplasts in mesophyll cells from the AtMinD1 overexpression lines was less than the number of proplastids present in the cells of the shoot apical meristem, it is believed that a disruption of both proplastid and chloroplast division in these plants occurred.

To confirm that the transgenic phenotypes resulted from overexpression of the endogenous AtminD1 gene, a northern blot of poly(A)$^+$RNA isolated from sense and wild type plants was performed using a radiolabeled RNA probe specific for AtMinD1. Total RNA was isolated from 23- to 27-day-old plants as described previously using 1 g of leaf tissue from independent transgenic lines (T$_3$) or from wild type to determine the expression levels of the AtMinD protein coding sequence. Only transgenic individuals exhibiting severely reduced numbers of chloroplasts for the AtMinD1 sense plants were used for RNA isolation. Northern blot analysis confirmed that the severe disruption in chloroplast division was accompanied by AtminD1 overexpression.

The remaining 19 (29%) T$_1$ individuals among the 71 that differed obviously from wild type had less severe defects in plastid division. Most of these resembled the antisense plants, having variable numbers and sizes of chloroplasts. It has not been determined whether this phenotype is indeed the result of AtMinD1 overexpression, although it parallels findings in *E. coli* that suggest overexpression of minD induces minicell formation. However, this phenotype is also consistent with cosuppression of endogenous AtMinD1 gene expression. The AtMinD1 sense lines grew somewhat more slowly and did not grow as large as the wild type or antisense plants. They also began flowering about 3 days earlier on average.

Taken together, these results indicate that either decreased or increased numbers of chloroplasts can be obtained in transgenic plants by manipulation of MinD expression levels. Manipulation of the size and shape of chloroplasts may also be obtained.

---

I claim:

1. A transgenic plant comprising in its genome an artificial genetic construct comprising a promoter which functions in cells of the plant operatively linked to a nucleic acid that encodes a MinD protein, wherein: (a) the nucleic acid is in the sense orientation, (b) expression of the nucleic acid in the plant causes alteration in the size, shape and/or number of plastids in plant cells of the plant as compared to non-transgenic plants of the species, and (c) the MinD protein has at least 92% sequence identity to SEQ ID NO:2.

2. The plant of claim 1, wherein the nucleic acid encodes an *Arabidopsis* MinD protein.

3. The plant of claim 1, wherein the the promoter is a CaMV 35S promoter and the construct further comprises an OCS terminator positioned 3' to the nucleic acid.

4. The plant of claim 3, wherein the nucleic acid encodes an *Arabidopsis* MinD protein.

5. The plant of claim 3, wherein the nucleic acid is SEQ ID NO:1.

6. The plant of claim 1, wherein the plastids are chloroplasts.

7. A transgenic plant comprising in its genome an artificial genetic construct comprising a promoter which functions in cells of the plant operatively linked to a nucleic acid encoding a MinD protein, wherein the nucleic acid is in the sense orientation wherein expression of the nucleic acid in the plant causes alteration in the size, shape and/or number of plastids in plant cells of the plant as compared to non-transgenic plants of the species, and wherein the nucleic acid is SEQ ID NO:1.

8. A transgenic plant comprising in its genome an artificial genetic construct comprising promoter that is functional in plants operatively linked to a nucleic acid encoding a MinD protein, wherein expression of the nucleic acid in the plant causes alteration in the size, shape and/or number of plastids in plant cells of the plant as compared to non-transgenic plants of the species, wherein the protein has the amino acid sequence of SEQ ID NO:2.

9. A seed of the plant of claim 1, wherein the seed comprises the artificial gene construct.

10. A plant seed comprising in its genome a genetic construct comprising a promoter that functions in a plant operatively linked to a nucleic acid that encodes a MinD protein, wherein the promoter is not natively associated with the nucleic acid wherein: (a) expression of the nucleic acid in the plant causes alteration in the size, shape and/or number of plastids in plant cells of the plant as compared to nontransgenic plants of the species, and (b) the MinD protein has at least 92% sequence identity to SEQ ID NO:2.

11. The plant seed of claim 10, wherein the nucleic acid encodes an *Arabidopsis* MinD protein.

12. The plant seed of claim 10, wherein the nucleic acid is SEQ ID NO:1.

13. The plant seed of claim 10, wherein the the promoter is a CaMV 355 promoter and the construct further comprises an OCS terminator positioned after the nucleic acid.

14. The plant seed of claim 13, wherein the nucleic acid encodes an *Arabidopsis* MinD protein coding sequence.

15. The plant seed of claim 13, wherein the nucleic acid is SEQ ID NO:1.

16. An isolated DNA sequence comprising SEQ ID NO:1.

17. A genetic construct comprising a nucleic acid encoding a MinD protein in either a sense or antisense orientation operatively linked to a promoter that promotes expression of the nucleic acid in plants, wherein the promoter is not natively associated with the nucleic acid, and wherein the MinD protein has at least a 92% sequence identity to SEQ ID NO:2.

18. The construct of claim 17, wherein the nucleic acid encodes an *Arabidopsis* MinD protein.

19. The construct of claim 17, wherein the nucleic acid is SEQ ID NO:1.

20. The construct of claim 17, wherein the promoter is a CaMV 355 promoter.

21. An isolated, nucleic acid comprising a plant MinD gene, wherein the MinD gene encodes a protein having at least a 92% sequence identity to SEQ ID NO:2.

22. The nucleic acid of claim 21, wherein the nucleic acid is SEQ ID NO:1.

23. A method for altering the size, shape and/or number of plastids in plant cells, wherein the method comprises constructing a genetic construct comprising promoter that is functional in plants operatively linked to a nucleic acid encoding a MinD protein, wherein the promoter is not natively associated with the nucleic acid and wherein the MinD protein has at least 92% sequence identity to SEQ ID NO:2 introducing the genetic construct into a plant, selecting a plant that has received a copy of the genetic construct, and growing the plant under conditions that allow expression of the nucleic acid, thereby producing a plant with altered size shape or number of plastids.

24. The method of claim 23, wherein the nucleic acid encodes an *Arabidopsis* MinD protein.

25. The method of claim 23, wherein the nucleic acid is SEQ ID NO:1.

* * * * *

SEQUENCE LISTING

<160> NUMBER OF SEQ ID NOS: 12

<210> SEQ ID NO 1
<211> LENGTH: 978
<212> TYPE: DNA
<213> ORGANISM: Prototheca wickerhamii
<220> FEATURE:
<221> NAME/KEY: CDS
<222> LOCATION: (1)..(978)

<400> SEQUENCE: 1

```
atg gcg tct ctg aga ttg ttc tca acg aat cat caa tct ctt ctc ctt        48
Met Ala Ser Leu Arg Leu Phe Ser Thr Asn His Gln Ser Leu Leu Leu
 1               5                  10                  15 cca tca tct ctc tca caa aag act cta ata tct tca cca aga ttc gtc        96
Pro Ser Ser Leu Ser Gln Lys Thr Leu Ile Ser Ser Pro Arg Phe Val
             20                  25                  30 aat aac cct agc aga cgg agt cca ata cga tcc gtt ctt caa ttt aat       144
Asn Asn Pro Ser Arg Arg Ser Pro Ile Arg Ser Val Leu Gln Phe Asn
         35                  40                  45 cgc aaa ccg gaa ctc gcc gga gaa acg ccg cgt atc gtc gtt atc acc       192
Arg Lys Pro Glu Leu Ala Gly Glu Thr Pro Arg Ile Val Val Ile Thr
     50                  55                  60 tcc gga aaa ggc ggt gtt gga aag acg aca acc acc gca aat gtc ggt       240
Ser Gly Lys Gly Gly Val Gly Lys Thr Thr Thr Thr Ala Asn Val Gly
 65                  70                  75                  80 ctc tct ctc gct cgt tac ggt ttc tca gtt gtc gcc att gac gcc gac       288
```

```
Leu Ser Leu Ala Arg Tyr Gly Phe Ser Val Val Ala Ile Asp Ala Asp
             85                  90                  95 ctt ggt ctc cgt aac ctc gat ctc ctc cta ggg tta gag aat cga gtc        336
Leu Gly Leu Arg Asn Leu Asp Leu Leu Leu Gly Leu Glu Asn Arg Val
            100                 105                 110 aat tac act tgc gtc gag gtt ata aac gga gat tgt cgt ctc gat caa        384
Asn Tyr Thr Cys Val Glu Val Ile Asn Gly Asp Cys Arg Leu Asp Gln
            115                 120                 125 gct ctg gta cgt gat aag cgt tgg tcg aat ttc gaa ttg cta tgt ata        432
Ala Leu Val Arg Asp Lys Arg Trp Ser Asn Phe Glu Leu Leu Cys Ile
    130                 135                 140 tct aaa cct aga tcg aaa ctt ccg atg gga ttt ggt ggt aaa gca ttg        480
Ser Lys Pro Arg Ser Lys Leu Pro Met Gly Phe Gly Gly Lys Ala Leu
145                 150                 155                 160 gaa tgg ctt gtg gat gcg ttg aaa act aga ccg gaa ggt tca ccg gat        528
Glu Trp Leu Val Asp Ala Leu Lys Thr Arg Pro Glu Gly Ser Pro Asp
                165                 170                 175 ttc atc atc atc gat tgt cct gca gga atc gat gcc gga ttc ata acc        576
Phe Ile Ile Ile Asp Cys Pro Ala Gly Ile Asp Ala Gly Phe Ile Thr
            180                 185                 190 gcc att act ccg gcg aat gaa gca gtt ctg gta aca act ccg gat ata        624
Ala Ile Thr Pro Ala Asn Glu Ala Val Leu Val Thr Thr Pro Asp Ile
            195                 200                 205 aca gcg tta agg gat gct gat agg gtt acg ggt ttg tta gaa tgc gat        672
Thr Ala Leu Arg Asp Ala Asp Arg Val Thr Gly Leu Leu Glu Cys Asp
    210                 215                 220 gga atc aga gat ata aag atg att gtg aac aga gtg aga act gat atg        720
Gly Ile Arg Asp Ile Lys Met Ile Val Asn Arg Val Arg Thr Asp Met
225                 230                 235                 240 att aaa gga gag gat atg atg tca gtg tta gat gtg cag gag atg ttg        768
Ile Lys Gly Glu Asp Met Met Ser Val Leu Asp Val Gln Glu Met Leu
                245                 250                 255 gga ttg tca ttg ctt ggt gta att cct gaa gat tct gag gtt att cga        816
Gly Leu Ser Leu Leu Gly Val Ile Pro Glu Asp Ser Glu Val Ile Arg
            260                 265                 270 agc acg aat cga ggg ttt ccg ctt gtt ctg aat aag cct cct acg ctt        864
Ser Thr Asn Arg Gly Phe Pro Leu Val Leu Asn Lys Pro Pro Thr Leu
            275                 280                 285 gcg gga ttg gcg ttt gag cag gcg gct tgg aga ctc gtt gag caa gat        912
Ala Gly Leu Ala Phe Glu Gln Ala Ala Trp Arg Leu Val Glu Gln Asp
    290                 295                 300 agt atg aag gct gtt atg gtg gag gaa gaa cct aag aaa cgt ggc ttc        960
Ser Met Lys Ala Val Met Val Glu Glu Glu Pro Lys Lys Arg Gly Phe
305                 310                 315                 320 ttc tct ttc ttt ggc ggc                                                978
Phe Ser Phe Phe Gly Gly
            325

<210> SEQ ID NO 2
<211> LENGTH: 326
<212> TYPE: PRT
<213> ORGANISM: Prototheca wickerhamii

<400> SEQUENCE: 2

Met Ala Ser Leu Arg Leu Phe Ser Thr Asn His Gln Ser Leu Leu Leu
 1               5                  10                  15

Pro Ser Ser Leu Ser Gln Lys Thr Leu Ile Ser Ser Pro Arg Phe Val
            20                  25                  30

Asn Asn Pro Ser Arg Arg Ser Pro Ile Arg Ser Val Leu Gln Phe Asn
        35                  40                  45
```

```
Arg Lys Pro Glu Leu Ala Gly Glu Thr Pro Arg Ile Val Val Ile Thr
     50                  55                  60

Ser Gly Lys Gly Gly Val Gly Lys Thr Thr Thr Ala Asn Val Gly
 65                  70                  75                  80

Leu Ser Leu Ala Arg Tyr Gly Phe Ser Val Val Ala Ile Asp Ala Asp
                 85                  90                  95

Leu Gly Leu Arg Asn Leu Asp Leu Leu Gly Leu Glu Asn Arg Val
             100                 105                 110

Asn Tyr Thr Cys Val Glu Val Ile Asn Gly Asp Cys Arg Leu Asp Gln
             115                 120                 125

Ala Leu Val Arg Asp Lys Arg Trp Ser Asn Phe Glu Leu Leu Cys Ile
    130                 135                 140

Ser Lys Pro Arg Ser Lys Leu Pro Met Gly Phe Gly Lys Ala Leu
145                 150                 155                 160

Glu Trp Leu Val Asp Ala Leu Lys Thr Arg Pro Glu Gly Ser Pro Asp
                165                 170                 175

Phe Ile Ile Ile Asp Cys Pro Ala Gly Ile Asp Ala Gly Phe Ile Thr
                180                 185                 190

Ala Ile Thr Pro Ala Asn Glu Ala Val Leu Val Thr Thr Pro Asp Ile
    195                 200                 205

Thr Ala Leu Arg Asp Ala Asp Arg Val Thr Gly Leu Leu Glu Cys Asp
    210                 215                 220

Gly Ile Arg Asp Ile Lys Met Ile Val Asn Arg Val Arg Thr Asp Met
225                 230                 235                 240

Ile Lys Gly Glu Asp Met Met Ser Val Leu Asp Val Gln Met Leu
                245                 250                 255

Gly Leu Ser Leu Leu Gly Val Ile Pro Glu Asp Ser Glu Val Ile Arg
                260                 265                 270

Ser Thr Asn Arg Gly Phe Pro Leu Val Leu Asn Lys Pro Thr Leu
                275                 280                 285

Ala Gly Leu Ala Phe Glu Gln Ala Ala Trp Arg Leu Val Glu Gln Asp
    290                 295                 300

Ser Met Lys Ala Val Met Val Glu Glu Glu Pro Lys Lys Arg Gly Phe
305                 310                 315                 320

Phe Ser Phe Phe Gly Gly
                325

<210> SEQ ID NO 3
<211> LENGTH: 1182
<212> TYPE: DNA
<213> ORGANISM: Tagetes erecta
<220> FEATURE:
<221> NAME/KEY: CDS
<222> LOCATION: (50)..(934)

<400> SEQUENCE: 3
aagcttgata tcgcaactcc ataactgatc ttcttcttct tctccggcg atg aca tcc        58
                                                     Met Thr Ser
                                                       1 ctg agg ttt cta aca gaa ccc tca ctt gta tgc tca tcc act ttc ccc        106
Leu Arg Phe Leu Thr Glu Pro Ser Leu Val Cys Ser Ser Thr Phe Pro
      5                  10                  15 aca ttc aat ccc cta cac aaa acc cta act aaa cca aca cca aaa ccc        154
Thr Phe Asn Pro Leu His Lys Thr Leu Thr Lys Pro Thr Pro Lys Pro
 20                  25                  30                  35 tac cca aag cca cca cca att cgc tcc gtc ctt caa tac aat cgc aaa        202
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Tyr | Pro | Lys | Pro | Pro | Ile | Arg | Ser | Val | Leu | Gln | Tyr | Asn | Arg | Lys |     |     |
|     |     |     | 40  |     |     |     | 45  |     |     |     | 50  |     |     |     |     |     |

```
cca gag ctc gcc gga gac act cca cga gtc gtc gca atc gac gcc gac      250
Pro Glu Leu Ala Gly Asp Thr Pro Arg Val Val Ala Ile Asp Ala Asp
            55                  60                  65 gtt ggt cta cgt aac ctc gat ctt ctt ctc ggt ctc gaa aac cgc gtc      298
Val Gly Leu Arg Asn Leu Asp Leu Leu Leu Gly Leu Glu Asn Arg Val
        70                  75                  80 aat tac acc gtc gtt gaa gtt ctc aac ggc gat tgc aga ctc gac caa      346
Asn Tyr Thr Val Val Glu Val Leu Asn Gly Asp Cys Arg Leu Asp Gln
    85                  90                  95 gcc cta gtt cgt gat aaa cgc tgg tca aat ttc gaa ttg ctt tgt att      394
Ala Leu Val Arg Asp Lys Arg Trp Ser Asn Phe Glu Leu Leu Cys Ile
100             105                 110                 115 tca aaa cct agg tca aaa ttg cct tta gga ttt ggg gga aaa gct tta      442
Ser Lys Pro Arg Ser Lys Leu Pro Leu Gly Phe Gly Gly Lys Ala Leu
                120                 125                 130 gtt tgg ctt gat gca tta aaa gat agg caa gaa ggt tgc ccg gat ttt      490
Val Trp Leu Asp Ala Leu Lys Asp Arg Gln Glu Gly Cys Pro Asp Phe
            135                 140                 145 ata ctt ata gat tgt cct gca ggt att gat gcc ggg ttc ata acc gcc      538
Ile Leu Ile Asp Cys Pro Ala Gly Ile Asp Ala Gly Phe Ile Thr Ala
        150                 155                 160 att aca ccg gct aac gaa gcc gta tta gtt aca aca cct gat att act      586
Ile Thr Pro Ala Asn Glu Ala Val Leu Val Thr Thr Pro Asp Ile Thr
    165                 170                 175 gca ttg aga gat gca gat aga gtt aca ggc ttg ctt gaa tgt gat gga      634
Ala Leu Arg Asp Ala Asp Arg Val Thr Gly Leu Leu Glu Cys Asp Gly
180                 185                 190                 195 att agg gat att aaa atg att gtg aac aga gtt aga act gat ttg ata      682
Ile Arg Asp Ile Lys Met Ile Val Asn Arg Val Arg Thr Asp Leu Ile
                200                 205                 210 agg ggt gaa gat atg atg tca gtt ctt gat gtt caa gag atg ttg gga      730
Arg Gly Glu Asp Met Met Ser Val Leu Asp Val Gln Glu Met Leu Gly
            215                 220                 225 ttg tca ttg ttg agt gat acc cga gga ttc gaa gtg att cgg agt acg      778
Leu Ser Leu Leu Ser Asp Thr Arg Gly Phe Glu Val Ile Arg Ser Thr
        230                 235                 240 aat aga ggg ttt ccg ctt gtg ttg aac aag cct ccg act tta gca gga      826
Asn Arg Gly Phe Pro Leu Val Leu Asn Lys Pro Pro Thr Leu Ala Gly
    245                 250                 255 ttg gca ttt gag cag gct gct tgg aga ttg gtt gag caa gat agc atg      874
Leu Ala Phe Glu Gln Ala Ala Trp Arg Leu Val Glu Gln Asp Ser Met
260                 265                 270                 275 aag gct gtg atg gtg gag gaa gaa cct aaa aag agg gga ttt ttc tcg      922
Lys Ala Val Met Val Glu Glu Glu Pro Lys Lys Arg Gly Phe Phe Ser
                280                 285                 290 ttt ttt gga ggt tagtgatcga attcgttgaa tcgttgagtt gggtttgttt         974
Phe Phe Gly Gly
            295 tggtggagaa atgtgtcttg tttgttcatg taggagctgc tatgtgtcac ttgaaatgtt   1034 atgtgtacag taagctgata aggattgttt taattcagtt ttcagagaga aaattagaat   1094 tgtagcaact tttcatttga tcaattcaat tgtatttctt tggttcagtg atgaattttt   1154 actcaaaatc aaaaaaaaaa aaaaaaaa                                      1182

<210> SEQ ID NO 4
<211> LENGTH: 295
<212> TYPE: PRT
```

<213> ORGANISM: Tagetes erecta

<400> SEQUENCE: 4

Met Thr Ser Leu Arg Phe Leu Thr Glu Pro Ser Leu Val Cys Ser Ser
1               5                   10                  15

Thr Phe Pro Thr Phe Asn Pro Leu His Lys Thr Leu Thr Lys Pro Thr
            20                  25                  30

Pro Lys Pro Tyr Pro Lys Pro Pro Ile Arg Ser Val Leu Gln Tyr
        35                  40                  45

Asn Arg Lys Pro Glu Leu Ala Gly Asp Thr Pro Arg Val Val Ala Ile
    50                  55                  60

Asp Ala Asp Val Gly Leu Arg Asn Leu Asp Leu Leu Gly Leu Glu
65                  70                  75                  80

Asn Arg Val Asn Tyr Thr Val Val Glu Val Leu Asn Gly Asp Cys Arg
                85                  90                  95

Leu Asp Gln Ala Leu Val Arg Asp Lys Arg Trp Ser Asn Phe Glu Leu
            100                 105                 110

Leu Cys Ile Ser Lys Pro Arg Ser Lys Leu Pro Leu Gly Phe Gly Gly
        115                 120                 125

Lys Ala Leu Val Trp Leu Asp Ala Leu Lys Asp Arg Gln Glu Gly Cys
130                 135                 140

Pro Asp Phe Ile Leu Ile Asp Cys Pro Ala Gly Ile Asp Ala Gly Phe
145                 150                 155                 160

Ile Thr Ala Ile Thr Pro Ala Asn Glu Ala Val Leu Val Thr Thr Pro
                165                 170                 175

Asp Ile Thr Ala Leu Arg Asp Ala Asp Arg Val Thr Gly Leu Leu Glu
            180                 185                 190

Cys Asp Gly Ile Arg Asp Ile Lys Met Ile Val Asn Arg Val Arg Thr
        195                 200                 205

Asp Leu Ile Arg Gly Glu Asp Met Met Ser Val Leu Asp Val Gln Glu
    210                 215                 220

Met Leu Gly Leu Ser Leu Leu Ser Asp Thr Arg Gly Phe Glu Val Ile
225                 230                 235                 240

Arg Ser Thr Asn Arg Gly Phe Pro Leu Val Leu Asn Lys Pro Pro Thr
                245                 250                 255

Leu Ala Gly Leu Ala Phe Glu Gln Ala Ala Trp Arg Leu Val Glu Gln
            260                 265                 270

Asp Ser Met Lys Ala Val Met Val Glu Glu Pro Lys Lys Arg Gly
        275                 280                 285

Phe Phe Ser Phe Phe Gly Gly
    290                 295

<210> SEQ ID NO 5
<211> LENGTH: 30
<212> TYPE: DNA
<213> ORGANISM: Artificial Sequence
<220> FEATURE:
<221> NAME/KEY: primer_bind
<222> LOCATION: (1)..(30)
<220> FEATURE:
<223> OTHER INFORMATION: Description of Artificial Sequence: pcr primer

<400> SEQUENCE: 5
ccgaattcga agcagcagca ctatcaatgg                                    30

<210> SEQ ID NO 6
<211> LENGTH: 28

```
<212> TYPE: DNA
<213> ORGANISM: Artificial Sequence
<220> FEATURE:
<223> OTHER INFORMATION: Description of Artificial Sequence: PCR primer

<400> SEQUENCE: 6
cggaattcga tccgtttgcc atttagcc                                              28

<210> SEQ ID NO 7
<211> LENGTH: 359
<212> TYPE: PRT
<213> ORGANISM: Prototheca wickerhamii

<400> SEQUENCE: 7
```

| Met | Asn | Lys | Leu | His | Tyr | Phe | Ile | Asn | Asn | Ile | Phe | Asn | Leu | Ile | Val |
|---|---|---|---|---|---|---|---|---|---|---|---|---|---|---|---|
| 1 |  |  |  | 5 |  |  |  |  | 10 |  |  |  |  | 15 |  |

| Tyr | Tyr | Leu | Tyr | Ser | Leu | Tyr | Phe | Lys | Glu | Asp | Lys | Ile | Lys | Arg | Arg |
|---|---|---|---|---|---|---|---|---|---|---|---|---|---|---|---|
|  |  |  | 20 |  |  |  |  | 25 |  |  |  |  | 30 |  |  |

| Leu | Ser | Asn | Met | Thr | Lys | Lys | Gln | Glu | Asn | Tyr | Asn | Lys | Glu | Gln | Leu |
|---|---|---|---|---|---|---|---|---|---|---|---|---|---|---|---|
|  |  | 35 |  |  |  |  | 40 |  |  |  |  | 45 |  |  |  |

| Ile | Lys | Glu | Lys | Pro | Glu | Glu | Arg | Lys | Ile | Ile | Lys | Glu | Gln | Leu | Glu |
|---|---|---|---|---|---|---|---|---|---|---|---|---|---|---|---|
|  | 50 |  |  |  |  | 55 |  |  |  |  | 60 |  |  |  |  |

| Gln | Leu | Ile | Gln | Lys | Pro | Ser | Glu | Ser | Glu | Tyr | Asn | Thr | Glu | Leu | Asp |
|---|---|---|---|---|---|---|---|---|---|---|---|---|---|---|---|
| 65 |  |  |  |  | 70 |  |  |  |  | 75 |  |  |  |  | 80 |

| Ile | Glu | Leu | Asp | Lys | Gly | Asp | Ser | Asp | Glu | Leu | Glu | Pro | Arg | Val | Ile |
|---|---|---|---|---|---|---|---|---|---|---|---|---|---|---|---|
|  |  |  |  | 85 |  |  |  |  | 90 |  |  |  |  | 95 |  |

| Val | Ile | Thr | Ser | Gly | Lys | Gly | Gly | Val | Gly | Lys | Thr | Thr | Thr | Thr | Ala |
|---|---|---|---|---|---|---|---|---|---|---|---|---|---|---|---|
|  |  |  | 100 |  |  |  |  | 105 |  |  |  |  | 110 |  |  |

| Asn | Leu | Gly | Met | Ser | Ile | Ala | Arg | Phe | Gly | Tyr | Arg | Val | Ala | Leu | Ile |
|---|---|---|---|---|---|---|---|---|---|---|---|---|---|---|---|
|  |  | 115 |  |  |  |  | 120 |  |  |  |  | 125 |  |  |  |

| Asp | Ala | Asp | Ile | Gly | Leu | Arg | Asn | Leu | Asp | Leu | Leu | Gly | Leu | Glu |
|---|---|---|---|---|---|---|---|---|---|---|---|---|---|---|
| 130 |  |  |  |  | 135 |  |  |  |  | 140 |  |  |  |  |

| Asn | Arg | Ile | Thr | Phe | Thr | Ala | Met | Asp | Ile | Ile | Glu | Gly | Arg | Cys | Arg |
|---|---|---|---|---|---|---|---|---|---|---|---|---|---|---|---|
| 145 |  |  |  |  | 150 |  |  |  |  | 155 |  |  |  |  | 160 |

| Leu | Asp | Gln | Ala | Leu | Val | Arg | Glu | Lys | Arg | Trp | Lys | Asn | Leu | Ala | Leu |
|---|---|---|---|---|---|---|---|---|---|---|---|---|---|---|---|
|  |  |  | 165 |  |  |  |  | 170 |  |  |  |  | 175 |  |  |

| Leu | Ala | Val | Ser | Lys | Asn | His | Gln | Lys | Tyr | Asn | Val | Thr | Gln | Gln | His |
|---|---|---|---|---|---|---|---|---|---|---|---|---|---|---|---|
|  |  |  | 180 |  |  |  |  | 185 |  |  |  |  | 190 |  |  |

| Met | Arg | Gln | Leu | Val | Phe | Ser | Ile | Lys | Glu | Leu | Gly | Ile | Asn | Ser | Ile |
|---|---|---|---|---|---|---|---|---|---|---|---|---|---|---|---|
|  |  | 195 |  |  |  |  | 200 |  |  |  |  | 205 |  |  |  |

| Leu | Ile | Asp | Cys | Pro | Ala | Gly | Ile | Asp | Val | Gly | Phe | Ile | Asn | Ala | Ile |
|---|---|---|---|---|---|---|---|---|---|---|---|---|---|---|---|
|  | 210 |  |  |  |  | 215 |  |  |  |  | 220 |  |  |  |  |

| Ala | Pro | Ala | Gln | Glu | Ala | Ile | Ile | Val | Thr | Thr | Pro | Glu | Ile | Thr | Ala |
|---|---|---|---|---|---|---|---|---|---|---|---|---|---|---|---|
| 225 |  |  |  |  | 230 |  |  |  |  | 235 |  |  |  |  | 240 |

| Ile | Arg | Asp | Ala | Asp | Arg | Val | Ala | Gly | Leu | Leu | Glu | Ala | Asn | Thr | Ile |
|---|---|---|---|---|---|---|---|---|---|---|---|---|---|---|---|
|  |  |  | 245 |  |  |  |  | 250 |  |  |  |  | 255 |  |  |

| Val | Asp | Thr | Lys | Leu | Leu | Leu | Asn | Arg | Val | Arg | Met | Asp | Met | Ile | Gln |
|---|---|---|---|---|---|---|---|---|---|---|---|---|---|---|---|
|  |  |  | 260 |  |  |  |  | 265 |  |  |  |  | 270 |  |  |

| Asn | Ser | Thr | Met | Leu | Ser | Ile | Met | Asp | Val | Gln | Glu | Thr | Leu | Gly | Ile |
|---|---|---|---|---|---|---|---|---|---|---|---|---|---|---|---|
|  |  | 275 |  |  |  |  | 280 |  |  |  |  | 285 |  |  |  |

| Pro | Leu | Leu | Gly | Ala | Ile | Pro | Glu | Asp | Thr | Asn | Val | Ile | Ile | Ser | Thr |
|---|---|---|---|---|---|---|---|---|---|---|---|---|---|---|---|
|  | 290 |  |  |  |  | 295 |  |  |  |  | 300 |  |  |  |  |

| Asn | Lys | Gly | Glu | Pro | Leu | Val | Leu | Asp | Lys | Lys | Leu | Thr | Leu | Ser | Gly |
|---|---|---|---|---|---|---|---|---|---|---|---|---|---|---|---|
| 305 |  |  |  |  | 310 |  |  |  |  | 315 |  |  |  |  | 320 |

| Ile | Ala | Phe | Glu | Asn | Ala | Ala | Arg | Arg | Leu | Ile | Gly | Lys | Glu | Asp | Tyr |
|---|---|---|---|---|---|---|---|---|---|---|---|---|---|---|---|
|  |  |  | 325 |  |  |  |  | 330 |  |  |  |  | 335 |  |  |

```
Phe Val Asp Leu Asp Ile Pro Thr Lys Ser Ile Ile Lys Lys Ile Gln
            340                 345                 350

Lys Phe Phe Trp Gly Glu Phe
        355

<210> SEQ ID NO 8
<211> LENGTH: 266
<212> TYPE: PRT
<213> ORGANISM: Synechocystis PCC6803

<400> SEQUENCE: 8

Met Asn Arg Ile Ile Val Val Thr Ser Gly Lys Gly Gly Val Gly Lys
  1               5                  10                  15

Thr Thr Thr Thr Ala Asn Leu Gly Ala Ala Leu Ala Arg Leu Gly Lys
             20                  25                  30

Lys Val Val Leu Ile Asp Ala Asp Phe Gly Leu Arg Asn Leu Asp Leu
         35                  40                  45

Leu Leu Gly Leu Glu Gln Arg Ile Val Tyr Thr Ala Ile Asp Val Leu
     50                  55                  60

Ala Asp Glu Cys Thr Ile Asp Lys Ala Leu Val Lys Asp Lys Arg Leu
 65                  70                  75                  80

Pro Asn Leu Val Leu Leu Pro Ala Ala Gln Asn Arg Ser Lys Asp Ala
                 85                  90                  95

Ile Asn Ala Glu Gln Met Gln Ser Leu Val Glu Gln Leu Lys Asp Lys
            100                 105                 110

Phe Asp Tyr Ile Ile Ile Asp Cys Pro Ala Gly Ile Glu Ala Gly Phe
        115                 120                 125

Arg Asn Ala Val Ala Pro Ala Gln Glu Ala Ile Ile Val Thr Thr Pro
    130                 135                 140

Glu Met Ser Ala Val Arg Asp Ala Asp Arg Val Ile Gly Leu Leu Glu
145                 150                 155                 160

Ala Glu Asp Ile Gly Lys Ile Ser Leu Ile Val Asn Arg Leu Arg Pro
                165                 170                 175

Glu Met Val Gln Leu Asn Gln Met Ile Ser Val Glu Asp Ile Leu Asp
            180                 185                 190

Leu Leu Ala Val Pro Leu Ile Gly Ile Leu Pro Asp Asp Gln Lys Ile
        195                 200                 205

Ile Ile Ser Thr Asn Lys Gly Glu Pro Leu Val Met Glu Glu Lys Leu
    210                 215                 220

Ser Val Pro Gly Leu Ala Phe Gln Asn Ile Ala Arg Arg Leu Glu Gly
225                 230                 235                 240

Gln Asp Ile Pro Phe Leu Asp Phe Met Ala Ala His Asn Thr Leu Leu
                245                 250                 255

Asn Arg Ile Arg Arg Arg Leu Leu Gly Gly
            260                 265

<210> SEQ ID NO 9
<211> LENGTH: 270
<212> TYPE: PRT
<213> ORGANISM: Guillardia theta

<400> SEQUENCE: 9

Met Ala Arg Ile Val Val Ile Thr Ser Gly Lys Gly Gly Val Gly Lys
  1               5                  10                  15

Thr Thr Val Thr Ala Asn Leu Gly Met Ala Leu Ala Gln Leu Gly Tyr
             20                  25                  30
```

```
Arg Thr Ala Leu Ile Asp Ala Asp Ile Gly Leu Arg Asn Leu Asp Leu
            35                  40                  45

Leu Leu Gly Leu Glu Asn Arg Val Ile Tyr Thr Ala Leu Glu Val Leu
    50                  55                  60

Ser Gly Glu Cys Arg Leu Glu Gln Ala Leu Ile Lys Asp Lys Arg Gln
 65              70                  75                  80

Pro Asn Leu Val Leu Leu Pro Ala Ala Gln Asn Arg Asn Lys Asp Ser
                    85                  90                  95

Val Thr Glu Glu Gln Met Lys Phe Leu Val Asn Leu Val Asn Lys
                100                 105                 110

Asp Tyr Asp Tyr Leu Leu Ile Asp Cys Pro Ala Gly Ile Glu Thr Gly
            115                 120                 125

Phe His Asn Ala Ile Gly Pro Ala Gln Glu Ala Ile Val Val Thr Thr
        130                 135                 140

Pro Glu Ile Ala Ala Val Arg Asp Ala Asp Arg Val Ile Gly Leu Leu
145                 150                 155                 160

Glu Ala Asn Gly Ile Lys Gln Ile Lys Leu Leu Val Asn Arg Leu Arg
                165                 170                 175

Pro Gln Met Val Lys Ala Asn Asp Met Met Ser Val Ala Asp Val Arg
                180                 185                 190

Glu Ile Leu Ala Ile Pro Leu Ile Gly Val Ile Pro Glu Asp Glu Cys
            195                 200                 205

Val Ile Val Ser Thr Asn Arg Gly Glu Pro Leu Val Leu Glu Lys Asn
210                 215                 220

Leu Ser Leu Pro Gly Leu Ala Phe Glu His Thr Ala Cys Arg Leu Asp
225                 230                 235                 240

Gly Gln Glu Ile Glu Phe Leu Asp Leu Gln Ser Tyr Ser Arg Gly Pro
                245                 250                 255

Leu Lys Arg Leu Arg Arg Phe Phe Leu Gly Ser Ser Thr Asn
                260                 265                 270

<210> SEQ ID NO 10
<211> LENGTH: 282
<212> TYPE: PRT
<213> ORGANISM: Chlorella vulgaris

<400> SEQUENCE: 10

Met Val Phe Ser Thr Gly Asn Gly Asp Asp Asn Ser Lys Gly Leu Glu
 1               5                  10                  15

Arg Val Ile Val Ile Thr Ser Gly Lys Gly Val Gly Lys Thr Thr
                 20                 25                  30

Thr Thr Ala Asn Leu Gly Met Ser Ile Ala Arg Leu Gly Tyr Arg Val
            35                  40                  45

Ala Leu Ile Asp Ala Asp Ile Gly Leu Arg Asn Leu Asp Leu Leu Leu
        50                  55                  60

Gly Leu Glu Asn Arg Val Leu Tyr Thr Ala Met Asp Ile Val Glu Gly
 65                  70                 75                  80

Gln Cys Arg Leu Asp Gln Ala Leu Ile Arg Asp Lys Arg Trp Lys Asn
                 85                 90                  95

Leu Ala Leu Leu Ala Ile Ser Lys Asn Arg Gln Lys Tyr Asn Val Thr
                100                 105                 110

Arg Lys Asn Met Gln Asn Leu Ile Asp Ser Val Lys Glu Leu Gly Phe
            115                 120                 125

Gln Phe Val Leu Ile Asp Cys Pro Ala Gly Ile Asp Val Gly Phe Ile
```

```
            130                 135                 140
Asn Ala Ile Ala Ser Ala Gln Glu Ala Val Ile Val Thr Thr Pro Glu
145                 150                 155                 160

Ile Thr Ala Ile Arg Asp Ala Asp Arg Val Ala Gly Leu Leu Glu Ala
                165                 170                 175

Asn Gly Ile Tyr Asn Val Lys Leu Leu Val Asn Arg Val Arg Pro Asp
            180                 185                 190

Met Ile Gln Lys Asn Asp Met Met Ser Val Arg Asp Val Gln Glu Met
        195                 200                 205

Leu Gly Ile Pro Leu Leu Gly Ala Ile Pro Glu Asp Thr Ser Val Ile
    210                 215                 220

Ile Ser Thr Asn Lys Gly Glu Pro Leu Val Leu Asn Lys Lys Leu Thr
225                 230                 235                 240

Leu Ser Gly Ile Ala Phe Glu Asn Ala Ala Arg Arg Leu Ile Gly Lys
                245                 250                 255

Gln Asp Tyr Phe Ile Asp Leu Thr Ser Pro Gln Lys Gly Met Phe Gln
            260                 265                 270

Lys Leu Gln Glu Phe Phe Leu Gly Glu Glu
        275                 280

<210> SEQ ID NO 11
<211> LENGTH: 274
<212> TYPE: PRT
<213> ORGANISM: Nephroselmis olivacea

<400> SEQUENCE: 11

Met Thr Met Gln Asp Lys Glu Pro Ser Ala Pro Ala Cys Arg Val Ile
  1               5                  10                  15

Val Ile Thr Ser Gly Lys Gly Gly Val Gly Lys Thr Thr Ala Thr Ala
                 20                  25                  30

Asn Leu Gly Met Cys Ile Ala Arg Leu Gly Tyr Arg Val Ala Leu Ile
             35                  40                  45

Asp Ala Asp Ile Gly Leu Arg Asn Leu Asp Leu Leu Leu Gly Leu Glu
         50                  55                  60

Asn Arg Val Val Tyr Thr Ala Met Glu Val Ile Glu Gly Gln Cys Arg
 65                  70                  75                  80

Leu Glu Gln Ala Leu Ile Arg Asp Lys Arg Trp Lys Asn Leu Ser Met
                 85                  90                  95

Leu Ala Met Ser Lys Asn Arg Gln Arg Tyr Asn Met Thr Arg Lys Asn
            100                 105                 110

Met Met Met Ile Val Asp Ser Ile Lys Glu Arg Gly Tyr Gln Tyr Ile
        115                 120                 125

Leu Ile Asp Cys Pro Ala Gly Ile Asp Ala Gly Phe Val Asn Ala Ile
    130                 135                 140

Ala Pro Ala Asp Glu Ala Ile Leu Val Thr Thr Pro Glu Ile Thr Ala
145                 150                 155                 160

Ile Arg Asp Ala Asp Arg Val Ala Gly Leu Leu Glu Ala Asn Asp Phe
                165                 170                 175

Tyr Asn Val Arg Leu Val Ala Asn Arg Val Arg Pro Glu Met Ile Gln
            180                 185                 190

Gln Asn Asp Met Met Ser Val Asp Asp Val Gln Gly Met Ile Gly Val
        195                 200                 205

Pro Leu Leu Gly Ala Ile Pro Glu Asp Lys Asn Val Ile Ile Ser Thr
    210                 215                 220
```

-continued

```
Asn Arg Gly Glu Pro Leu Val Cys Gln Lys Thr Ile Thr Leu Ala Gly
225                 230                 235                 240

Val Ala Phe Glu Glu Ala Ala Arg Arg Leu Val Gly Leu Pro Ser Pro
                245                 250                 255

Ser Asp Ser Ala Pro Ser Arg Gly Trp Phe Ala Ala Ile Arg Arg Leu
                260                 265                 270

Trp Ser
```

<210> SEQ ID NO 12
<211> LENGTH: 162
<212> TYPE: PRT
<213> ORGANISM: Oryza sativa

<400> SEQUENCE: 12

```
Met Ala Phe Ala Pro Arg Leu Leu Leu Pro Ser Arg Cys Pro Pro Pro
1               5                   10                  15

Ala Ser Ser Pro Ala Arg His Gly Gly Arg Thr Ala Pro Glu Leu Ser
                20                  25                  30

Gly Pro Thr Pro Arg Val Val Val Thr Ser Gly Lys Gly Gly Val
            35                  40                  45

Gly Lys Thr Thr Thr Ala Asn Leu Ala Ala Ser Leu Ala Arg Leu
    50                  55                  60

Ser Leu Ser Ala Val Ala Val Asp Ala Asp Ala Gly Leu Arg Asn Leu
65              70                  75                  80

Asp Leu Leu Gly Leu Glu Asn Arg Val His Leu Thr Ala Ala Asp
            85                  90                  95

Val Leu Ala Gly Asp Cys Arg Leu Asp Gln Ala Leu Val Arg His Arg
            100                 105                 110

Ala Leu His Asp Leu Gln Leu Leu Cys Leu Ser Lys Pro Arg Ser Lys
            115                 120                 125

Leu Pro Leu Ala Phe Gly Ser Lys Thr Leu Thr Trp Val Ala Asp Ala
    130                 135                 140

Leu Arg Arg Ala Ala Asn Pro Pro Ala Phe Ile Leu Ile Asp Cys Pro
145                 150                 155                 160

Ala Gly
```